United States Patent [19]

Foery et al.

[11] 4,045,459
[45] Aug. 30, 1977

[54] AGENT FOR THE REGULATION OF PLANT GROWTH

[75] Inventors: Werner Foery, Basel; Hanspeter Fischer, Bottmingen; Dieter Lohmann, Pratteln; Gerd Greber, Binningen, all of Switzerland

[73] Assignee: Ciba-Geigy Corporation, Ardsley, N.Y.

[21] Appl. No.: 709,827

[22] Filed: July 29, 1976

Related U.S. Application Data

[63] Continuation of Ser. No. 447,402, March 1, 1974, abandoned, which is a continuation-in-part of Ser. No. 278,890, Aug. 9, 1972, abandoned.

[51] Int. Cl.² ........................... C07F 7/04; C07F 7/18
[52] U.S. Cl. ........................... 260/448.8 R; 71/79
[58] Field of Search ........................... 260/448.8 R

[56] References Cited

U.S. PATENT DOCUMENTS

| 3,008,975 | 11/1961 | Schubert | 260/448.8 R |
| 3,390,977 | 7/1968 | Leasure et al. | 71/79 |
| 3,390,978 | 7/1968 | Leasure et al. | 71/85 |
| 3,413,329 | 11/1968 | Pepe et al. | 260/448.8 R X |
| 3,694,480 | 9/1972 | Omietanski | 260/448.8 R X |
| 3,928,406 | 12/1975 | Leeper et al. | 260/448.8 R |

FOREIGN PATENT DOCUMENTS

| 837,649 | 3/1970 | Canada | 260/448.8 R UX |
| 802,969 | 10/1958 | United Kingdom | 260/448.8 R UX |
| 949,126 | 2/1964 | United Kingdom | 260/448.8 R UX |

OTHER PUBLICATIONS

"J. Med. Chem." 9, p. 949 (1966).
"J.A.C.S.", 68, p. 485 (1946).
"J.A.C.S.", 70, p. 2869 (1948).

*Primary Examiner*—Paul F. Shaver
*Attorney, Agent, or Firm*—Harry Falber

[57] ABSTRACT

The present invention relates to new compositions and methods for the regulation of plant growth, especially for fruit abscission, acceleration of ripening and latex discharge and to new active substances of the class of β-halogenoethyl-methyl-silanes.

The active substances in the new compositions respond to the formula

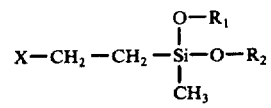

wherein X is chlorine or bromine, each of the radicals $R_1$ and $R_2$ independently represent substituted or unsubstituted alkyl radicals, alkenyl, halogenalkenyl, alkynyl and cycloalkyl radicals, substituted or unsubstituted phenyl and benzyl radicals; one or each of the symbols $R_1$ and $R_2$ can also represent the group —$COR_3$ wherein $R_3$ stands for an unsubstituted or substituted alkyl or alkenyl radical, a possible phenyl substituent being itself substituted or not, for an alkynyl, alkoxyalkyl, alkoxycarbonylalkyl, benzoylalkyl or phenyl radical the latter being optionally substituted or for a heterocyclic radical; $R_1$ and $R_2$, also with the signification of —$COR_3$ can also form together with the adjacent atoms a silicon-containing heterocyclic ring system.

The β-bromoethyl-methyl-silanes (X=Br) of the above formula and all those β-chloroethyl-methyl-silanes (X=Cl) wherein not both radicals $R_1$ and $R_2$ represent the methyl group, are new compounds.

7 Claims, No Drawings

AGENT FOR THE REGULATION OF PLANT GROWTH

CROSS-REFERENCE

This is a continuation of application Ser. No. 447,402, filed Mar. 1, 1974, now abandoned, which, in turn, is a continuation-in-part of application Ser. No. 278,890, filed Aug. 9, 1972, now abandoned.

DETAILED DISCLOSURE

The present invention relates to compounds, compositions and a method for the regulation of plant growth, for the purpose of improving crop yield and facilitating harvesting of agricultural, forestry and horticultural products, by the use of β-halogenoethyl-silanes as active substances; and also to new β-halogenoethyl-methyl-silanes and to processes for the production of these silanes.

It has been found that the β-halogenoethyl-methyl-silanes of this invention have a surprisingly favorable action on the growth and differentiation of parts and tissues of plants above and below the soil. They are in some respects superior to the plant-growth regulator 2-chloroethanephosphonic acid, known from the prior art, which is a similar active substance with respect to its mode of action, and they thus constitute a valuable technical advance.

The β-halogenethyl-methyl-silanes correspond to formula I

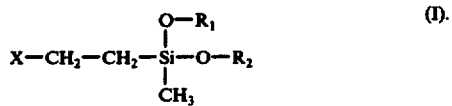

The symbols in this formula have the following meanings: X represents chlorine or bromine, and $R_1$ and $R_2$ are independently of each other $C_2$–$C_{18}$ unsubstituted alkyl or $C_1$–$C_{18}$ alkyl radicals substituted by halogen, cyano, $C_1$–$C_8$ alkoxy $C_1$–$C_8$ alkylthio, $C_3$–$C_6$ alkenyloxy, $C_2$–$C_8$ alkoxy carbonyl, $C_2$–$C_8$ alkoxy alkoxy, $C_3$–$C_8$ alkylthio, $C_3$–$C_{12}$ cycloalkyl phenoxy, a 5 or 6 membered heterocyclic ring or a di- or tri $C_1$–$C_4$ alkyl ammonio group;

$C_3$–$C_{18}$ alkenyl radicals unsubstituted or substituted by halogen or $C_3$–$C_{12}$ cycloalkyl or phenyl;

$C_3$–$C_8$ alkynyl radicals, unsubstituted or substituted by halogen;

$C_3$–$C_{12}$ cycloalkyl or cyloalkenyl radicals;

phenyl radicals, unsubstituted or mono-or polysubstituted by halogen, cyano, nitro, formyl, trifluoromethyl, $C_1$–$C_4$ alkyl, $C_1$–$C_4$ alkoxy, $C_2$–$C_6$ alkoxycarbonyl and/or $C_1$–$C_4$ alkylthio;

benzyl radicals unsubstituted or mono-or polysubstituted in the phenyl ring by halogen, cyano, nitro, $C_1$–$C_4$ alkyl, $C_1$–$C_4$ alkoxy and/or alkylthio;

or the group — CO — $R_3$ wherein $R_3$ represents a $C_1$–$C_{18}$ alkyl, $C_2$–$C_8$ alkenyl radical $C_3$–$C_8$ alkinyl radical, which alkyl and alkenyl radicals may be unsubstituted or substituted by halogen, $C_3$–$C_{12}$ cycloalkyl or phenyl, unsubstituted or mono-or polysubstituted by halogen, cyano, nitro, $C_1$–$C_4$ alkyl, $C_1$–$C_4$ alkoxy or $C_1$–$C_4$ alkylthio; a $C_2$–$C_8$ alkoxyalkyl, $C_2$–$C_8$ alkoxycarbonyl a benzoyl-$C_1$–$C_4$-alkyl radical; or a phenyl radical, unsubstituted or mono or polysubstituted by halogen, cyano, nitro, $C_1$–$C_4$ alkyl, $C_1$–$C_4$ alkoxy, $C_1$–$C_4$ alkylthio, or a 5 to 6 membered heterocyclic radical; or $R_1$ and $R_2$, when being CO—$R_3$ can form together with the ajacent Si-atom a saturated or unsaturated heterocyclic ring system.

This formula may be broken down into the following subgroups: β-Halogenoethyl-methyl-silanes formula I wherein X represents chlorine or bromine and $R_1$ and $R_2$ are identical and represent $C_1$–$C_{18}$ alkyl radicals unsubstituted $C_1$–$C_{18}$ alkyl radicals or substituted by halogen, cyano, $C_1$–$C_8$ alkoxy, $C_1$–$C_8$ alkylthio, $C_3$–$C_6$ alkenyloxy, $C_2$–$C_8$ alkylcarbonyl, $C_2$–$C_8$ alkoxyalkoxy, $C_3$–$C_{12}$ Cycloalkyl, phenoxy, a 5 to 6 membered heterocyclic ring or a di- or tri-$C_1$–$C_4$-alkyl ammonio group.

β-Halogenoethyl-methyl-silanes according to formula I wherein X represents chlorine or bromine and $R_1$ and $R_2$ are identical and represent $C_3$–$C_{18}$ alkenyl radicals, unsubstituted or substituted by halogen $C_3$–$C_{12}$ cycloalkyl or phenyl.

β-Halogenoethyl-methyl-silanes according to formula I, wherein X represents chlorine or bromine and $R_1$ and $R_2$ are identical and represent $C_3$–$C_8$ alkinyl radicals unsubstituted or substituted by halogen.

β-Halogenoethyl-methyl-silanes according to formula I, wherein X represents chlorine or bromine and $R_1$ and $R_2$ are identical and represent $C_3$–$C_{12}$ cycloalkyl or cycloalkenyl radicals.

β-Halogenoethyl-methyl-silanes according to formula I, wherein X represents chlorine or bromine and $R_1$ and $R_2$ identical and represent phenyl, unsubstituted or mono-or polysubstituted by halogen, cyano, nitro, formyl, trifluoromethyl, $C_1$–$C_4$ alkyl, $C_1$–$C_4$ alkoxy, $C_2$–$C_6$ alkoxycarbonyl or $C_1$–$C_4$ alkylthio.

β-Halogenoethyl-methyl-silanes according to formula I wherein X represents chlorine or bromine and $R_1$ and $R_2$ are identical and represent benzyl radicals, unsubstituted or mono or polysubstituted in the phenyl ring by halogen, cyano, nitro, $C_1$–$C_4$ alkyl, $C_1$–$C_4$ alkoxy or $C_1$–$C_4$ alkylthio.

β-Halogenoethyl-methyl-silanes according to the formula

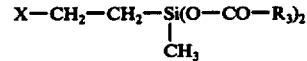

wherein $R_3$ X represents chlorine or bromine and $R_3$ represents a $C_1$–$C_{18}$ alkyl, $C_2$–$C_8$ alkinyl radical, which alkyl and alkenyl radicals may be substituted by halogen, $C_3$–$C_8$ cycloalkyl or phenyl unsubstituted or mono- or polysubstituted by halogen, cyano, nitro, $C_1$–$C_4$ alkyl, $C_1$–$C_4$ alkoxy or $C_1$–$C_4$ alkylthio; a $C_2$–$C_8$ alkoxyalkyl, $C_2$–$C_8$ alkoxycarbonyl; a benzoyl-$C_1$–$C_4$-alkyl radical or a phenyl radical that is unsubstituted or mono-or polysubstituted by halogen, cyano, nitro $C_1$–$C_4$ alkyl, $C_1$–$C_4$ alkoxy or $C_1$–$C_4$ alkylthio or a 5 to 6 membered heterocyclic ring or both —OCOR$_3$ together with the silicium atom form a saturated or unsaturated heterocyclic radical ring system.

β-Halogenoethyl-methyl-silanes according to the formula

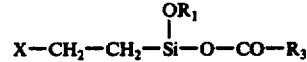

wherein X, $R_1$ and $R_3$ have the meanings given above.

By alkyl radicals in formula I are meant straight-chain or branched radicals having 1 to 18 carbon atoms, such as, e.g., methyl, ethyl, n-propyl, isopropyl, n-butyl, sec-butyl, n-hexyl, n-octyl, n-dodecyl, n-octadecyl, etc.

The straight-chain and branched alkyl radicals having 1 to 8 carbon atoms are particularly preferred, and they form also the alkyl moiety of alkoxy, alkylthio, di- and trialkylammonio, or of alkoxycarbonyl substituents of an alkyl radical or of a phenyl radical. Halogenalkyl radicals are alkyl radicals which can be substituted by fluorine, chlorine and/or /bromine, such as, e.g., trifluoromethyl, 2-chloroethyl, 6-chlorohexyl, etc. By alkenyl radicals are meant, in formula I, straight-chain or branched radicals having 3 to 18 carbon atoms, e.g., propenyl, butenyl, octenyl, decenyl, heptadecenyl radicals. These alkenyl radicals can be mono- or polysubstituted by halogens, such as fluorine, chlorine, bromine and/or iodine. Alkenyl radicals having 3 to 6 carbon atoms from the alkenyl moiety of alkenyloxy radicals. Alkynyl radicals preferably contain 3 to 8 carbon atoms in a straight chain, such as, e.g. 2-propynyl, 2-butynyl or 3-hexynyl. By cycloaliphatic radicals are meant mono- or polycyclic cycloalkyl ro cycloalkenyl radicals having 3 to 12 carbon atoms, such as, e.g., cyclopropyl, cyclopentyl, cyclopentenyl, cyclohexenyl, bicyclohexenyl, which may be mono- or polysubstituted by methyl groups.

Five- or six-membered heterocyclic radicals $R_3$, or these as substituents of alkyl radicals $R_1$ and $R_2$, can contain 1 to 2 hetero atoms, especially nitrogen and/or /oxygen. Heterocyclic ring systems containing the Si atom, which are formed by the radicals $R_1$ and $R_2$ including the type —$COR_3$, can be saturated or unsaturated; the hydrocarbon bridge is therefore alkylene or alkenylene.

To be mentioned as anions of di- and trialkylammonio radicals (which can be regarded as being salt forms of a dialkylamino radical) are particularly those of hydrohalic acids, alkylsulphonic acids and alkylphosphoric acids.

The $\beta$-halogenoethyl-silanes of formula I affect in a varying manner the growth of parts of plants above and below the soil, and in the usual concentrations in which they are applied they have low toxicity towards warm-blooded animals. In these concentrations, the active substances produce no morphological changes or damage which would result in a withering of the plant. The compounds are not mutagenic. Their action differs from that of a herbicidal active substance and that of a fertiliser. The action corresponds more to the effects which can be observed on application of ethylene to various parts of plants. It is known that also the plant itself produces, in various stages of development, ethylene to a varying extent, particularly before and during the ripening process of the fruits, and at the end of the vegetation period as the abscission of the fruit and leaves occurs. Since the regulation of ripening and of fruit and leaf abscission by chemical substances is of the greatest commercial significance for the cultivation of fruit, citrus fruit, pineapples and cotton, attempts have been made to exert a favourable external influence on the development of the plant by application of ethylene-releasing agents. Various classes of substances have meanwhile become known, with which certain such effects can be obtained.

Such known compounds are either relatively unstable under the effects of weather, because they are very susceptible to hydrolysis, or they are phytotoxic. $\beta$-Halogenoethylphosphonic acid derivatives are described in the South African Pat. No. 68/1036 as active substances regulating plant growth. These compounds decompose in and on the plant with the release of ethylene, and are therefore similar in action and in range of action to ethylene. By virtue of their very low stability, phosphonic acid derivatives are not able, however, to satisfy the demands made on them. As they are stable only in an acid medium, more precisely in a pH-range below 5, the cencentrates of active substance have to be stabilised by the addition of acids. This addition of acid limites, however, the range of application of these active substances with regard to phytotoxic effects. Furthermore, the storage of such sensitive concentrates of active substance presents difficulties.

Also known as herbicidal active substances, are halogenalkyl-methyl-silanes, cp., U.S. Pat. Nos. 3,390,976 and 3,390,977, and J.K. Leasure et al., J.Med. Chem. 9, 949 (1966). $\beta$-Chloroethyl(methyl-dimethoxy)silane was prepared by J. K. Leasure et al. (loc.cit.), but it has no herbicidal action.

The U.S. Pat. No. 3,183,076 describes $\alpha$-chloroethyl-methyldialkoxy-silanes which can be used for the promotion of germination power, leaf abscission, etc.

The present invention relates to new agents containing, as active substance, $\beta$-halogenoethyl-methyl-silanes, the said new agents having a stimulating or a retarding effect on plant growth in the various stages of development of the plants. By virtue of the very good stability of the active substances of fomula I, these agents contain, apart from the usual carriers, distributing agents, and stabilizers protecting against the effects of light and of oxidation, no stabilizing acid-additive, and they therefore have an unlimited field of application. The new agents act on the physiological processes of plant development, and can be employed for various purposes in connection with improved crop yield, with facilitation of harvesting and with economy of labor in the field of cultivation techniques. The extremely varied effects of these active substances depend essentially on the point of time of application in relation to the stage of development of the seed or of the plant, as well as on the applied concentrations.

By a suitable treatment with the compounds according to the invention, the ripening process in plants can be accelerated and, at the same time, a better and more uniform ripening of fruit or of other harvested crops attained, factors which, in the case of various types of fruit, etc., e.g., pineapples, tomatoes, tobacco, and other cultivated crops, are of great economical importance.

It has been found that the compounds of formula I are particularly suitable for the control of fruit abscission. The gathering of fruits, such as, e.g., olives, citrus fruits, cherries, apples, damsons, nuts and berries (currants, grapes, gooseberries, bilberries, cranberries, etc.) is conventionally done by hand. As part of the process of rationalization in agriculture, other methods for the harvesting of fruit have been proposed. Very diverse mechanical devices have been developed for this purpose. Plants and harvested crops are, however, damaged as a rule by this type of mechanical equipment. It has been discovered that fruit can be caused to fall either without mechanical aids or with a minimum of such aid, and consequently harvested more economically, when the trees, bushes and plants are treated, before ripening of the fruit, with the active substances according to the invention.

The promotion of fruit abscission can moreover be utilized in such a manner that, as a result of prompt application of the active substances, a chemically effected thinning of the young fruit is obtained. This is desirable in the case of too dense a natural fruit setting, such as frequently occurs, for example, with apples, peaches or citrus fruits.

The vegetative plant growth and the germination power are influenced by the new agents; and the blossom formation, the development of the fruit and the formation of separating tissues promoted. There occurs also a strengthening of the support tissues of the stalks of the treated plants. The formation of undesirable side shoots is very greatly reduced on various types of plants, such as, e.g., on tobacco and on azalea plants; and the vegetative growth in the case of grapevines is inhibited. The new compounds also have a secretion-promoting action, e.g., the latex discharge is promoted in the case of *Hevea brasiliensis*, an effect of considerable commercial importance. Tests have shown that the rooting of seedlings and cuttings, as well as the development of tubers of potatoes, is promoted. In addition, there occurs a simultaneous sprouting of dormat rhizomes, which is particularly important in the case of various perennial weeds, such as couchgrass, Johnson grass and cyperus, which can then be easily destroyed or suppressed by herbicides. The germination capacity of seeds is promoted with low concentrations, and prevented with higher concentrations. Both these factors are commercially important. A control of the blossoming time and of the number of blossoms is possible with many ornamental and cultivated plants. This effect is especially important in connection with pineapples. If all the plants concerned blossom simultaneously, then the crops can be gathered within a comparatively short space of time. With regard to *cucurbitaceae* and other plants, there occurs a shifting of blossom sex differentiation in favor of female blossoms. The influencing of blossom sex differentiation can have a potential use in practice, e.g., as an aid in the case of hybridization in seed cultivation, or for the increasing of crop yield, e.g., in the growing of *cucurbitaceae*.

By virtue of the control of blossom formation, of blossom sex and of vegetative growth, the active substances used according to the invention can appreciably increase the crop yield of plants (e.g., fruit, seeds, leaves).

The growth of shoots and roots can be regulated by the active substances to an extent governed by the level of concentration of these substances. It is thus possible to inhibit the growth of plants. One economic advantage of this is, for example, the slowing down of rate of growth of grass along the edges of streets and paths, or on lawns, the required frequency of mowing or cutting being consequently reduced.

Seed germination, sprouting of buds and rhizomes, as well as formation of side shoots, are processes which can be promoted or inhibited by the stated active substances to a degree dependent on the applied concentration thereof. It is thus possible to promote the germination of seed and the sprouting of dormat rhizomes in the case of weeds, which facilitates the subsequent destruction of these weeds by means of herbicides. On the other hand, the undesired formation of side shoots on cut tobacco plants can be prevented.

To be emphasized also is the possibility in the case of certain plants of initiating leaf fall by application of the substances according to the invention. The harvesting of cotton plants is thus greatly facilitated where the cotton plants are defoliated beforehand by means of these compounds. And when plants have to be transplanted, transpiration can be reduced by defoliation.

Tests have also shown that a blossom and fruit thinning occurs on fruit trees. Furthermore, in the case of, for example, oranges, melons, apricots, preaches, tomatoes, bananas, bilberries, figs, coffee, pepper and pineapples fruit ripening and fruit coloration are accelerated and improved. And likewise the ripening of tobacco leaves is accelerated and improved. Fruit abscission is rendered appreciably easier by the formation of abscission tissue. This factor is of great commercial importance in mechanical harvesting, e.g., of citrus fruits such as oranges, grapefruits, or olives; or stone fruit such as cherries, damsons, peaches, plums, apricots; or pomaceous fruit such as apples and pears; or berries such as currants, raspberries and bilberries; or nuts such as walnuts and pecan nuts; or sub-tropical fruits such as coffee, figs and pepper. By suitable application of the above-mentioned substances, it is possible in the case of various cultivated crops, such as cotton, French beans, garden peas, ornamental shrubs, as well as seedlings, to effect defoliation, which likewise is of great commercial importance.

The extent and the nature of the action are dependent on the most diverse factors, particularly on the time of application with regard to the stage of development of the plant, and on the application concentration. These factors vary, however, depending on the type of plant and on the desired effect. Thus, for example, lawns are treated during the entire growth period; ornamental plants, of which, e.g., the intensity and number of the blossoms are to be increased, before development of the blossom setting; plants of which the fruit is to be sold, or in some other way utilised, at an appropriate interval of time before the gathering of the crop. Application of the active substances is effected by the use of solid or liquid agents, these being applied to parts of plants above the soil, to the surface of the soil, as well as into the soil itself. The preferred method is the application to the parts of plants above the soil, for which purpose solutions or aqueous suspensions are most suitable. In addition to solutions and dispersions for the treatment of the growth substrate (soil), dusts, granulates and scattering agents are also suitable.

Agents according to the invention are produced in a manner known per se by the intimate mixing and grinding of active substances of the general formula I with suitable carriers, optionally with the addition of dispersing agents or solvents which are inert to the active substances.

Water-dispersible concentrates of active substance, i.e., wettable powders, pastes and emulsion concentrates, are active substance concentrates which can be diluted with water to obtain any desired concentration. They consist of active substance, carrier, optionally additives which stabilize the active substance, surface-active substances, and anti-foam agents and, optionally, solvents. The concentration of active substance in these agents is 0.5 – 80%.

The wettable powders and pastes are obtained by the mixing and grinding of the active substances with dispersing agents and pulverulent carriers, in suitable devices, until homogeneity is attained. Suitable carriers are, e.g., the following:
kaolin, talcum, bole, loess, chalk, limestone, ground limestone, Attaclay, dolomite, diatomaceous earth, precipitated silicic acid, alkaline-earth silicates, sodium and potassium aluminum silicates (feldspar and mica), calcium and magnesium sulphates, magnesium oxide, ground synthetic materials, fertilizers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

Suitable dispersing agents are, e.g., the following:
condensation products of sulphonated naphthalene and sulphonated naphthalene derivatives with formaldehyde, condensation products of naphthalene or of naphthalenesulphonic acids with phenol and formaldehyde, as well as alkali, ammonium and alkaline-earth metal salts of ligninsulphonic acid, also alkylarylsulphonates, alkali metal salts and alkaline-earth metal salts of dibutylnaphthalenesulphonic acid, fatty alcohol sulphates such as salts of sulphated hexadecanols, heptadecanols, octadecanols, and salts of sulphated fatty alcohol glycol ether, the sodium salt of oleyl methyl tauride, ditertiary acetylene glycols, dialkyl dilauryl ammonium chloride, and fatty acid alkali-metal and alkaline-earth metal salts.

To these mixtures may also be added additives stabilizing the active substance, and/or non-ionic, anion-active and cation-active substances, which, for example, improve the adhesiveness of the active substances on plants and on parts of plants (adhesives and agglutinants), and/or ensure a better wettability (wetting agents). Suitable adhesives are, for example, the following:
olein/lime mixture, cellulose derivatives (methyl cellulose, carboxymethyl cellulose), hydroxyethylene glycol ethers of mono- and dialkylphenols having 5 - 15 ethylene oxide radicals per molecule and 8 - 9 carbon atoms in the alkyl radical, ligninsulphonic acid, alkali metal and alkaline-earth metal salts thereof, polyethylene glycol ethers (carbowaxes), fatty alcohol polyglycol ethers having 5 - 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea/formaldehyde, as well as latex products. The active substances are so mixed, ground, sieved and strained with the above mentioned additives that the solid constituent in the case of wettable powders has a particle size not exceeding 0.02 to 0.04 mm, and in the case of pastes not exceeding 0.03 mm.

Emulsion concentrates and pastes are prepared by application of the dispersing agents such as those mentioned in the preceding paragraphs, organic solvents and water. Suitable solvents are, e.g., the following:
ketones, benzene, xylenes, toluene, dimethylsulphoxide, and mineral oil fractions boiling in the range of 120° to 350°. The solvents must be practically odourless, non-phytotoxic, and inert to the active substances.

Furthermore, the agents according to the invention can be employed in the form of solutions. For this purpose, the active substance (or several active substances) of the general formula I is (or are) dissolved in suitable organic solvents, solvent mixtures, or water. The following can be used as organic solvents: aliphatic and aromatic hydrocarbons, chlorinated derivatives thereof, alkylnaphthalenes, or mineral oils on their own or in admixture with each other. The solutions should contain the active substances in a concentration range of 1 to 20%.

The solid preparations, such as dusts, scattering agents and granulates, contain solid carriers such as those mentioned in the foregoing, and, optionally, additives stabilizing the active substance. The particle size of the carriers is for dusts advantageously up to about 0.1 mm; for scattering agents from about 0.075 mm to 0.2 mm; and for granulates 0.2 mm or coarser. The concentrations of active substance in the solid preparations are from 0.5 to 80%.

All the mentioned active substance concentrates may also contain agents stabilizing against the effects of light, and antioxidants.

One of the β-halogen-ethyl-silanes embraced by formula I has already been described (J. K. Leasure et al., loc. cit.), namely, 2-chloroethyl-(methyl-dimethoxy)silane.

All other β-halogen-ethyl-methyl-silanes embraced by formula I are, on the other hand, new compounds, i.e., all in which $R_1$ and $R_2$ do not stand for methyl radicals if X represents chlorine.

The new β-halogen-ethyl-silanes of formula I are produced according to the present invention by reaction of a β-halogen-ethyl-methyl-dichlorosilane of formula II:

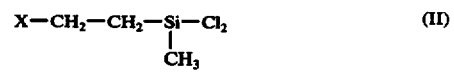
(II)

with two equivalents of an acid of formula III:

(III), or of a carboxylic acid anhydride of formula IV:

(IV)

to give a compound of formula V:

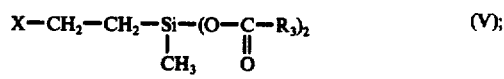
(V);

and, optionally, stepwise substitution of one or two of the radicals

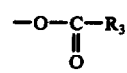

by radicals of alcohols of formula VI or VII

| $R_1OH$ | (VI) |
| $R_2OH$ | (VII). |

If the radicals $R_1$ and $R_2$ do not represent

then β-halogen-ethyl-methyl-silanes of formula I can be produced according to a variant of the process by the reaction of a β-halogen-ethyl-methyl-dichlorosilane of formula II with one equivalent of each, or two equivalents of one, of the alcohols of formulae VI or VII.

In formula II for the starting materials, X represents chlorine or bromine; $R_3$ in formulae III and IV, and $R_1$ and $R_2$ in formulae VI and VII, have the meanings given under formula I.

The process is preferably carried out in the presence of solvents and/or diluents which are inert to the reactants. Aprotic solvents are particularly suitable, such as, e.g., aliphatic and aromatic hydrocarbons, e.g., hexane, cyclohexane, benzene, toluene, xylene, halogenated hydrocarbons such as chlorinated ethylenes, carbon tetrachloride, chloroform, chlorobenzene, also ethers and ethereal compounds such as diethyl ether, tetrahydrofuran, etc.

For the attainment of a complete reaction, it is also possible for the alcohols, carboxylic acids and carboxylic acid anhydrides employed as reactants to serve, when used in excess, as solvents or diluents.

Furthermore, it may be necessary in some cases to add to the reaction mixture an acid-binding agent. Suitable for this purpose are, in particular, tertiary amines such as trialkylamines, e.g., triethylamine, pyridine and pyridine bases, dialkylanilines, etc.

The reaction temperatures are in the range of 0 to 100° C; the reaction duration can be from a few minutes to several days, and depends to a great extent on the reactivity of the alcohols employed.

Of the two starting materials of formula II, the chlorine compound, in which X therefore represents chlorine, is known and can be produced, e.g., by reaction of ethyl-(methyl-dichloro)-silane with chlorine (cp. J. K. Leasure et al. loc. cit.).

The starting material of formula II wherein X denotes bromine has not been hitherto described in the literature. This β-bromoethyl-methyl-dichlorosilane is produced by methods known per se by reaction of ethyl-(methyl-dichloro silane with bromine, corresponding to the process described by K. W. Michael (J. org. Chem 34 2822 (1969) for the production of β-bromoethyl-trichlorosilane; or by HBr-addition to vinyl-methyl-dichlorsilane, analogously to a mode of reaction given by A. I. Bourne (J.Chem. Soc., Sect. C, 1970 1740). UV-Light, peroxides and radical initiators can serve as catalysts for these addition reactions.

The following examples illustrate the invention in more detail. The β-halogenoethyl-methyl-silanes of formula I produced according to the examples, as well as others produced by the procedure described in the examples, are listed in the attached table.

The temperatures are expressed in degrees centigrade and the pressures in Torr; percentages are given by weight if not otherwise stated.

EXAMPLE 1

(Production of compounds)

An amount of 43 g of 2-chloroethyl-(methyl-dichloro)-silane is dissolved in 56 g of acetic acid anhydride; the solution is then allowed to stand in a closed vessel for 21 hours at room temperature. The reaction product is concentrated in vacuo. There is thus obtained an amount of 36.5 g of 2-chloroethyl-(methyl-diacetyloxy)-silane, B.P.: 71°-73°/0.8 Torr, $n_D^{20}$ = 1.4369.

EXAMPLE 2

An amount of 19.3 g of 2-chloroethyl-(methyl-diacetyloxy)-silane is dissolved in 40 ml of absolute benzene; to the solution are then added at 50°, within 60 minutes, 10.8 g of benzyl alcohol in 20 ml of absolute benzene. Stirring is carried out for 4½ hours at 50°-55°. The reaction mixture is evaporated in vacuo to obtain 11.0 g of 2-chloroethyl-(methyl-acetyloxy-benzyloxy)-silane, B.P.: 105°-110°/0.03 Torr, $n_D^{20}$ = 1.4963.

EXAMPLE 3

An amount of 35.5 g of 2-chloroethyl-(methyl-dichloro)-silane is dissolved in 350 ml of absolute diethyl ether; to the obtained solution are then added at −5° − −10°, within 5 minutes, 43.2 g of benzyl alcohol, and subsequently, within 30 minutes, 31.6 g of absolute pyridine dissolved in 100 ml of absolute ether. The mixture is stirred for a further hour at 0°, and then for 18 hours with refluxing.

The reaction mixture is filtered, the filtrate quickly washed with ice-cold water, dried, and concentrated in vacuo. Thus obtained are 52.9 g of 2-chloroethyl-(methyl-dibenzoxy)-silane, B.P.: 138°-141°/0.005 Torr, $n_{20}^D$ = 1.5339.

EXAMPLE 4

19.6 g of 3-hexyn-1-ol are dissolved in 200 ml of absolute diethyl ether; the solution is cooled to −10° − −5° and to it are added 15.8 g of absolute pyridine and then dropwise at the same temperature, within one hour, a solution of 17.7 g of 2-chloroethyl-(methyl-dichloro)-silane in 50 ml of absolute diethyl ether. The mixture is then stirred for 1 hour at 0°, for 2 hours at room temperature, and for 18 hours with refluxing. The reaction mixture is afterwards filtered, the filtrate quickly washed with ice-cold water, dried, and concentrated in vacuo. In this manner are obtained 22.5 g of 2-chloroethyl-(methyl-dihexynyl-(3')-oxy)-silane; B.P.: 190°-195°/0.005 Torr; $n_D^{20}$ = 1.4695.

EXAMPLE 5

(Production of a starting material)

An amount of 42.3 g of vinylmethyldichlorosilane is cooled to −5° to 0°; at this temperature is then introduced, with exposure to UV-radiation, hydrobromic acid for a period of 30 to 45 minutes. After the HBr-absorption is completed, the solution is allowed to stand overnight at room temperature under a nitrogen atmosphere. Thus obtained are 61.6 g of the new compound: 2-bromoethyl(methyl-dichloro)-silane, B.P.: 94°-96°/57 Torr.

EXAMPLE 6

(Production of a starting material)

A mixture of 142.3 g of vinylmethyldichlorosilane and 1 g of anhydrous $AlCl_3$ is cooled to −5° to 0°. At this temperature is introduced, with exposure to UV-radiation, hydrochloric acid for a period of 90 minutes. After the HCl-absorption is completed, the product is distilled under 0.1 Torr with a bath temperature of at most 15° in a flask cooled with dry ice. In this manner are obtained 177.5 g of the known 2-chloroethyl(methyl-dichloro)-silane, B.P.: 82° − 84°/68 Torr.

Compounds of formula I

Table I $$X-CH_2-CH_2-\underset{\underset{CH_3}{|}}{\overset{\overset{O-R_1}{|}}{Si}}-OR_2$$

| No. | $R_1 = R_2$ | X | Physical data M.P.; B.P./Torr; $n_D$ |
|---|---|---|---|
| 1 | Methyl | Cl | B.P.: 77° /25 |
| 2 | Methyl | Br | B.P.: 90–91° /25 |
| 3 | Ethyl | Cl | B.P.: 84–86° /16 |
| 4 | Ethyl | Br | B.P.: 94–96° /20 |
| 5 | iso-Propyl | Cl | B.P.: 88–90° /14 |
| 6 | Propyl | Cl | |
| 7 | Butyl | Cl | B.P.: 92–95° /0,3 |
| 8 | 2-Methylpropyl | Cl | |
| 9 | 1-Methylpropyl | Cl | B.P.: 72° /0,3 |
| 10 | Pentyl | Cl | B.P.: 135° /0,5 |
| 11 | 2-Methylbutyl | Cl | |
| 12 | 3-Methylbutyl | Cl | |
| 13 | Hexyl | Cl | B.P.: 135–140° /0,05 |
| 14 | Hexyl | Br | $n_D^{20}$ = 1,4484 |
| 15 | Heptyl | Cl | B.P.: 155–160° /0,05 |
| 16 | 2-Ethylhexyl | Cl | $n_D^{20}$ = 1,4441 |
| 17 | 1-Methylheptyl | Cl | $n_D^{20}$ = 1,4408 |
| 18 | Octyl | Cl | B.P.: 134° /0,001 |
| 19 | Octyl | Br | B.P.: 146° /0,001 |
| 20 | Nonyl | Cl | $n_D^{20}$ = 1,4446 |
| 21 | 1-Methyl-4-Ethylhexyl | Cl | |
| 22 | Decyl | Cl | $n_D^{20}$ = 1,4446 |
| 23 | Undecyl | Cl | |
| 24 | Dodecyl | Cl | $n_D^{20}$ = 1,4517 |
| 25 | Dodecyl | Br | $n_D^{20}$ = 1,4592 |
| 26 | Tetradecyl | Cl | |
| 27 | Hexadecyl | Cl | M.P.: 26–31° |
| 28 | Octadecyl | Cl | M.P.: 26–30° |
| 29 | Octadecyl | Br | M.P.: 30° |
| 30 | 2-Chloroethyl | Cl | B.P.: 121–125° /0,001 |
| 31 | 6-Chloroethyl | Cl | B.P.: 150–156° /0,001 |
| 32 | 2-Methoxyethyl | Cl | B.P.: 100–105° /0,001 |
| 33 | 2-Ethoxyethyl | Cl | B.P.: 104–108° /0,001 |
| 34 | 2-Butyloxyethyl | Cl | $n_D^{20}$ = 1,4411 |
| 35 | 2-Allyloxyethyl | Cl | B.P.: 125–130° /0,001 |
| 36 | 2-(1-Methylethenoyl-Oxy)ethyl | Cl | $n_D^{20}$ = 1,4578 |
| 37 | 2-Propyloxyethyl | Cl | |
| 38 | 2-i-Propyloxyethyl | Cl | |
| 39 | 2-Heexyloxyethyl | Cl | |
| 40 | 2-(2-Butyloxyethoxy)ethyl | Cl | B.P.: 138° /0,2 |
| 41 | 2-(2-(1-Undecylcarboxy)ethoxy)ethyl | Cl | |
| 42 | 2-(2-(1-Heptadecylcarboxy)ethoxy)-ethyl | Cl | |
| 43 | 2-(2-ethoxyethoxy)ethyl | Cl | $n_D^{20}$ = 1,4442 |
| 44 | 2-Phenoxyethyl | Cl | $n_D^{20}$ = 1,5311 |
| 45 | 2-Ethylthioethyl | Cl | B.P.: 160–165° /0,001 |
| 46 | 2-Octylthioethyl | Cl | $n_D^{20}$ = 1,4822 |
| 47 | 1-Phenylethyl | Cl | $n_D^{20}$ = 1,5179 |
| 48 | 3-Phenylpropyl | Cl | $n_D^{20}$ = 1,5211 |
| 49 | 2-Propenyl | Cl | B.P.: 50–54° /0,15 |
| 50 | 2-Butenyl | Cl | B.P.: 100–107° /0,55 |
| 51 | 2-Butenyl | Br | B.P.: 94–96° /0,005 |
| 52 | 3,7-Dimethyl-6-octenyl | Cl | $n_D^{20}$ = 1,4647 |
| 53 | 3,7-Dimethyl-2,6-octadienyl | Cl | $n_D^{20}$ = 1,4797 |
| 54 | 10-Undecenyl | Cl | |
| 55 | 9-Octadecenyl | Cl | $n_D^{20}$ = 1,4644 |
| 56 | 2-Propinyl | Cl | B.P.: 64–70° /0,1 |
| 57 | 2-propinyl | Br | B.P.: 98–100° /0,005 |
| 58 | 2-Butinyl | Cl | $n_D^{20}$ = 1,4762 |
| 59 | 3-Hexinyl | Cl | B.P.: 190–195° /0,005 |
| 60 | 1-Ethinylbutyl | Cl | |
| 61 | 3-Chloro-2-butenyl | Cl | B.P.: 105–110° /0,001 |
| 62 | 3-Phenyl-2-propenyl | Cl | $n_D^{20}$ = 1,5632 |
| 63 | 3-Phenyl-2-propenyl | Br | $n_D^{20}$ = 1,5741 |
| 64 | 2-Cyanoethyl | Cl | $n_D^{20}$ = 1,4598 |
| 65 | Ethpxycarbonylmethyl | Cl | |
| 66 | Butoxycarbonylmethyl | Cl | $n_D^{20}$ = 1,4478 |
| 67 | 1-Ethoxycarbonyl(1-methyl)methyl | Cl | |
| 68 | Cyclohexyl | Cl | B.P.: 120–125° /0,001 |
| 69 | Cyclohexylmethyl | Cl | B.P.: 118–123° /0,001 |
| 70 | Cyclohexylmethyl | Br | $n_D^{20}$ = 1,4845 |
| 71 | 3-Cyclohexylpropyl | Cl | $n_D^{20}$ = 1,4634 |
| 72 | 3,4-Dimethylcyclohexyl | Cl | $n_D^{20}$ = 1,4707 |
| 73 | 3,5-Dimethylcyclohexyl | Cl | $n_D^{20}$ = 1,4647 |
| 74 | 4-tert.Butylcyclohexyl | Br | |
| 75 | (−)Bornyl | Cl | M.P.: 55–58° |
| 76 | 6,6-Dimethylbicyclo 3.1.1. hept-2-ene-2-ethyl | Cl | |
| 77 | Benzyl | Cl | B.P.: 138–141° /0,005 |
| 78 | Benzyl | Br | B.P.: 130–154° /0,01 |
| 79 | 4-Chlorobenzyl | Cl | $n_D^{20}$ = 1,5434 |
| 80 | 4-Chlorobenzyl | Br | $n_D^{20}$ = 1,5554 |
| 81 | 4-Methoxybenzyl | Cl | $n_D^{20}$ = 1,5375 |
| 82 | 2,4-Dichlorobenzyl | Cl | $n_D^{20}$ = 1,5704 |
| 83 | 4-Methylbenzyl | Cl | $n_D^{20}$ = 1,5291 |
| 84 | Phenyl | Cl | $n_D^{20}$ = 1,5393 |
| 85 | 4-Chlorophenyl | Cl | $n_D^{20}$ = 1,5503 |
| 86 | 3-Chlorophenyl | Cl | $n_D^{20}$ = 1,5506 |
| 87 | 3,4-Dichlorophenyl | Cl | M.P.: 43–47° |
| 88 | 3,5-Dichlorophenyl | Cl | M.P.: 54–56° |
| 89 | 4-Bromophenyl | Cl | $n_D^{20}$ = 1,5760 |
| 90 | 4-Methoxyphenyl | Cl | $n_D^{20}$ = 1,5436 |
| 91 | 3-Methoxyphenyl | Br | $n_D^{20}$ = 1,5528 |
| 92 | 3-Methoxyphenyl | Cl | $n_D^{20}$ = 1,5425 |
| 93 | 4-Butyloxyphenyl | Cl | $n_D^{20}$ = 1,5212 |
| 94 | 3-tert.Butylphenyl | Cl | $n_D^{20}$ = 1,5230 |
| 95 | 3-Methylphenyl | Cl | $n_D^{20}$ = 1,5300 |
| 96 | 3-Methylphenyl | Br | $n_D^{20}$ = 1,5461 |
| 97 | 3,4-Dimethylphenyl | Cl | $n_D^{20}$ = 1,5346 |
| 98 | 3-Formylphenyl | Cl | M.P.: 91–93° |
| 99 | 4-Cyanophenyl | Cl | M.P.: 90–93° |
| 100 | 4-Ethoxycarbonylphenyl | Cl | M.P.: 94–96° |
| 101 | 3-Ethoxycarbonylphenyl | Cl | $n_D^{20}$ = 1,5275 |
| 102 | 3-Trifluoromethylphenyl | Cl | $n_D^{20}$ = 1,4676 |
| 103 | tetrahydropyranyl-CH$_2$— | Cl | $n_D^{20}$ = 1,4710 |
| 104 | furanyl-CH$_2$— | Cl | |
| 105 | thiophenyl-CH$_2$— | Cl | $n_D^{20}$ = 1,5490 |
| 106 | tetrahydrofuranyl-CH$_2$— | Cl | $n_D^{20}$ = 1,4670 |
| 107 | 1,3-dioxanyl (5-CH$_3$, 5-CH$_2$—) | Cl | |
| 108 | 2,2-dimethyl-1,3-dioxolanyl-CH$_2$— | Cl | $n_D^{20}$ = 1,4510 |

Table II $$R_1 = R_2 = -CO-R_3$$

| No. | $R_3$ is: | X | Physical data |
|---|---|---|---|
| 109 | Methyl | Cl | B.P.: 71–73°/0,8 |
| 110 | Methyl | Br | B.P.: 80–81°/0,3 |
| 111 | Ethyl | Cl | B.P.:81–82°/0,2 |
| 112 | Ethyl | Br | B.P.:93–96°/0,01 |
| 113 | iso-Propyl | Cl | B.P.:75°/0,08 |
| 114 | Pentyl | Cl | $n_D^{20}$ = 1,4302 |
| 115 | 1-Methylpentyl | Br | |
| 116 | 1-Ethylpentyl | Cl | |
| 117 | Heptyl | Cl | $n_D^{20}$ = 1,4340 |
| 118 | Octyl | Cl | |
| 119 | Undecyl | Cl | M.P.: 37° |
| 120 | Undecyl | Br | M.P.: 37–39° |
| 121 | Tridecyl | Br | |
| 122 | Pentadecyl | Cl | |
| 123 | Heptadecyl | Cl | M.P.: 64° |
| 124 | 2-Propenyl | Cl | $n_D^{20}$ = 1,4540 |
| 125 | 1-Propenyl | Cl | M.P.: 46–48° |
| 126 | 2-Propenyl | Br | $n_D^{20}$ = 1,4401 |
| 127 | 1,3-Pentadienyl | Cl | M.P.: 125–127° |
| 128 | 9-Decenyl | Cl | $n_D^{20}$ = 1,4640 |
| 129 | 8,11-Heptadecadienyl | Cl | $n_D^{20}$ = 1,4700 |

Table II-continued $R_1 = R_2 = -CO-R_3$

| No. | $R_3$ is: | X | Physical data |
|---|---|---|---|
| 130 | Chloromethyl | Cl | M.P.: 43–45° |
| 131 | Iodomethyl | Cl | M.P.: 35–38° |
| 132 | 2-Chloroethyl | Cl | $n_D^{20} = 1,4550$ |
| 133 | 1-Bromopentyl | Cl | $n_D^{20} = 1,4690$ |
| 134 | 10-Bromodecyl | Cl | M.P.: 42–45° |
| 135 | 10-Bromodecyl | Br | M.P.:37–39° |
| 136 | cis-2-Chloroethenyl | Cl | |
| 137 | cis-2-Chloroethenyl | Br | |
| 138 | Benzyl | Cl | M.P.: 39–41° |
| 139 | Benzyl | Br | M.P.: 68–70° |
| 140 | 4-Chlorobenzyl | Cl | M.P.: 96–102° |
| 141 | 3-Methylbenzyl | Cl | M.P.: 45–51° |
| 142 | 2-Phenyl ethyl | Cl | M.P.: 67–68° |
| 143 | 3-(4'-Methoxyphenyl)-ethyl | Cl | M.P.: 97–100° |
| 144 | 4-Ethoxycarbonylbutyl | Cl | $n_D^{21} = 1,4308$ |
| 145 | 3-Oxobutyl | Cl | |
| 146 | 3-Oxobutyl | Br | |
| 147 | 5-Phenyl-5-oxopentyl | Cl | M.P.: 75–77° |
| 148 | 2-Ethoxyethyl | Cl | $n_D^{20} = 1,4440$ |
| 149 | 3-Phenoxypropyl | Cl | |
| 150 | 2,4-Dichlorophenoxymethyl | Cl | M.P.: 125–127° |
| 151 | 2,4-Dichlorophenoxymethyl | Br | M.P.: 129–131° |
| 152 | 2-(4'-Chlorophenyl)-1- | Cl | |
| 153 | 2-Phenyl-1-ethenyl | Cl | M.P.: 123–124° |
| 154 | 2-Phenyl-1-ethenyl | Br | M.P.: 119–122° |
| 155 | 2-(3',4'-Dichlorophenyl)-1-ethenyl | Cl | M.P.: 187–195° |
| 156 | 2-(4'-Methoxyphenyl)-1-ethenyl | Cl | M.P.: 168–169° |
| 157 | Cyclohexylmethyl | Cl | $n_D^{20} = 1,4530$ |
| 158 | Cyclohexylmethyl | Br | $n_D^{20} = 1,4888$ |
| 159 | Cyclohexyl | Cl | $n_D^{20} = 1,4620$ |
| 160 | Cyclopropyl | Cl | $n_D^{20} = 1,4502$ |
| 161 | 3-Cyclohexenyl | Cl | $n_D^{20} = 1,4385$ |
| 162 | 3-Cyclohexenyl | Br | $n_D^{20} = 1,4748$ |
| 163 | 2-Cyclopentenyl-1-methyl | Cl | $n_D^{20} = 1,4652$ |
| 164 | 2-Cyclopentenyl-1-methyl | Br | $n_D^{20} = 1,5084$ |
| 165 | Phenyl | Cl | |
| 166 | 4-Chlorophenyl | Br | |
| 167 | 4-Methoxyphenyl | Cl | |
| 168 | 4-Methylphenyl | BR | |
| 169 | | Cl | |
| 170 | | B | |
| 171 | | Br | |

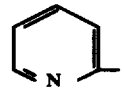
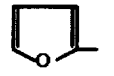
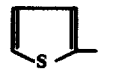

Table III $R_2 = -CO-R_3$

| No. | $R_1$ | $R_3$ is | X | Physical data |
|---|---|---|---|---|
| 172 | Benzyl | Methyl | Cl | B.P.: 105–14 110°/0,03 |
| 173 | Benzyl | Methyl | Br | B.P.: 140–147°/0,01 |
| 174 | Ethyl | Methyl | Cl | B.P.: 42°/0,5 |
| 175 | Pentyl | Methyl | Br | B.P.: 87°/0,0001 |
| 176 | Octyl | Methyl | Cl | B.P: 105–110°/0,005 |
| 177 | 2-Butinyl | Methyl | Cl | B.P.: 76–80°/0,02 |
| 178 | 2-Butenyl | Methyl | Cl | B.P.: 78–80°/0,02 |
| 179 | 4-Chlorobenzyl | Ethyl | Cl | B.P.: $n_D^{20} = 1,4974$ |
| 180 | 4-Chlorobenzyl | Ethyl | Br | $n_D^{20} = 1,5155$ |
| 181 | 3,7-Dimethyl-6-octenyl | Ethyl | Cl | $n_D^{20} = 1,4532$ |
| 182 | 4-Methoxybenzyl | Ethyl | Cl | $n_D^{20} = 1,4762$ |

Table IV

| No. | $R_1$ | $R_2$ | X | Anion | Physical data |
|---|---|---|---|---|---|
| 183 | 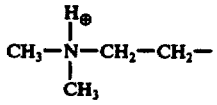 | Hexyl | Cl | Cl⁻ | $n_D^{20} = 1,4690$ |
| 184 | 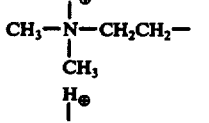 | Benzyl | Cl | Cl⁻ | M.P.: 33–40° |
| 185 | 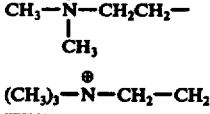 | Ethyl | Cl | Cl⁻ | M.P.: 38–42 |
| 186 |  | Ethyl | Cl | Cl⁻ | |

Table v

Compounds in which $R_1$ and $R_2$ together with the adjacent atoms from a Si-containing heterocycle:

| No. | Compound | Physical data |
|---|---|---|
| 187 | 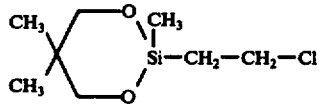 | B.P.: 155–160 |
| 188 | 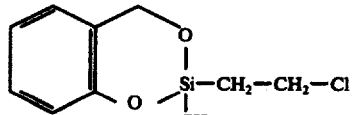 | M.P.: 108° |
| 189 | 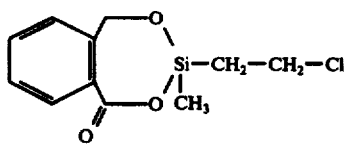 | $n_D^{20} = 1,4711$ |

Table v-continued

Compounds in which $R_1$ and $R_2$ together with the adjacent atoms from a Si-containing heterocycle:

| No. | Compound | Physical data |
|---|---|---|
| 190 | (structure: O=C-O-Si(CH₃)(CH₂-CH₂-Cl)-O-C=C ring) | |
| 191 | (structure: O=C-O-Si(CH₃)(CH₂-CH₂-Cl)-O-C-C ring) | |
| 192 | (structure: O=C-O-Si(CH₃)(CH₂-CH₂-Cl)-O-C ring) | $n_D^{25} = 1.4633$ |

EXAMPLE 7

(abscission tests)

a. Abscission of bean leaves in vitro

Segments of bean leaves of the type "Tempo" were immersed in a solution of 0.002% of active substance; for each active substance; for each active substance, 4–8 segments were left for 6 days in the active substance solution under controlled conditions. On specific days after the commencement of the treatment, the number of resulting abscissions (contraction or necking of the stalk in the abscission zone on the leaf-side) was assessed.

Tests with solutions containing the following active substance produced excellent results:
- (18) 2-chloroethyl-(methyl-dioctyloxy)-silane,
- (19) 2-bromoethyl-(methyl-dioctyloxy)-silane,
- (77) 2-chloroethyl-(methyl-dibenzyloxy)-silane,
- (78) 2-bromoethyl-(methyl-dibenzyloxy)-silane,
- (56) 2-chloroethyl-(methyl-dipropynyl-(2')-oxy)-silane,
- (50) 2-chloroethyl-(methyl-dibutenyl)-(2'-oxy)-silane,
- (81) 2-chloroethyl-(methyl)-di-4'-methoxybenzoxy)-silane,
- (109) 2-chloroethyl-(methyl-diacetoxy)-silane,
- (85) 2-chloroethyl-(methyl-di-4'-chlorobenzoxy)-silane,
- (30) 2-chloroethyl-(methyl-di-2'-chloroethoxy)-silane,
- (59) 2-chloroethyl-(methyl-di-hexynyl-(3')-oxy)-silane.

b. Abcission of oranges

The active substances were sprayed, in the form of solutions in concentrations of 0.2% and 0.4%, respectively, on to branches, well hung with fruit, of various orange trees. The tests were evaluated after 14 days according to the method developed by W. C. Wilson and C. H. Hendershott, [Proc. Am. Soc. Hort. Sc. 90, 123 – 129 (1967)]. The test consists of measuring the force in kilogram required for the abscission of the fruit.

The precise test procedure was as follows:

On orange trees of the below given variety, certain branches carrying at least 15 to 20 ripe oranges were sprayed with an agent having active substance concentrations of 0.4% and 0.2%, respectively. Seven days after application, the applied picking force required in the case of 10 similarly treated oranges was determined with the aid of a spring balance, and the average of the 10 values recorded.

The agents containing the following active substances of formula I were used in this test, in which the following tabulated plucking forces in kg* were measured, and the given percentage reductions of required plucking forces determined, the latter values being obtained on the basis of a comparative test carried out on fruit on untreated trees.

| Active substance No. | Concentration % | Plucking force in kg* | Plucking force reduction in % | Orange variety |
|---|---|---|---|---|
| 18 | 0,4 | 3,2 | 66% | Navel |
|    | 0,2 | 6,9 | 25% | |
| 19 | 0,4 | 0 | | |
|    | 0,2 | 0 | 100% fruit fall | Hamlin |
| 77 | 0,4 | <0,5 | >95% | |
|    | 0,2 | <0,5 | >95% | |
| 78 | 0,4 | <0,5 | >95% | Hamlin |
|    | 0,2 | <0,5 | >95% | |
| 13 | 0,4 | <0,5 | >95% | Hamlin |
| 24 | 0,4 | <0,5 | >95% | Hamlin |
|    | 0,2 | <0,5 | >95% | |
| 28 | 0,4 | 3,8 | 55% | Hamlin |
| 184 | 0,4 | 0 | 100% fruit | Hamlin |

| Active substance No. | Concentration % | Plucking force in kg* | Plucking force reduction in % | Orange variety |
|---|---|---|---|---|
| | 0,2 | <0,5 | fall >95% | Hamlin |

Plucking force <0.5 kg* denotes that the fruit can be so easily removed that no further measurement of the required force could be obtained.

c. Abscission of olives

On olive trees of the kind Zorzalena, groups of branches were sprayed with aqueous suspensions of the active substances. The concentration of the suspensions was 2000 and 4000 ppm of the compound to be tested. Some groups of branches were left untreated in order to serve as control. At the point of harvest, the olives were caused to fall by evenly shaking the different groups of branches by hand. The evaluation was made by counting the number of fallen olives and the number of fruits still on the branches. In the following table the results are summarized. The number of olives fallen for a given compound and concentration is given in percent.

| Compound No. | Percent of olives fallen at a concentration of | |
|---|---|---|
| | 4000 ppm | 2000 ppm |
| Control | 5% | |
| ETHREL* | 55% | 55% |
| 13 | 96% | 81% |
| 18 | 100% | 96% |
| 19 | 100% | 99% |
| 24 | 97% | 95% |
| 28 | 58% | 68% |
| 77 | 100% | 80% |
| 78 | 97% | 93% |

*Ethrel is 2-chloroethyl-phosphonic acid, known from the South African Patent No. 68/1036.

A similar experiment was run on olive trees of the kind Hjiblanca. The concentration of active substance was uniformely 2000 ppm.

| Compound No. | Percent of olives fallen at the concentration of 2000 ppm |
|---|---|
| Control | 15% |
| Ethrel | 70% |
| 2 | 90% |
| 3 | 88% |
| 4 | 83% |
| 5 | 100% |
| 7 | 84% |
| 24 | 96% |
| 33 | 86% |
| 45 | 93% |
| 48 | 88% |
| 49 | 85% |
| 61 | 95% |
| 66 | 82% |
| 68 | 81% |
| 69 | 80% |
| 77 | 98% |
| 79 | 80% |
| 81 | 98% |
| 82 | 100% |
| 83 | 100% |
| 90 | 99% |
| 92 | 96% |
| 95 | 86% |
| 103 | 84% |
| 109 | 83% |

EXAMPLE 8
(formulations)

Granulate

The following substances are used for the preparation of a 5% granulate:

5 parts of 2-chloroethyl-(methyl-di-2'-chloroethoxy) silane,
0.25 parts of epichlorohydrin,
0.25 parts of cetyl polyglycol ether,
3.50 parts of polyethylene glycol ("carbowax"),
91 parts of kaolin (particle size 0.2 – 0.8 mm).

The active substance is mixed with epichlorohydrin and the mixture dissolved in 6 parts of acetone; to the solution are then added polyethylene glycol and cetyl polyglycol ether. The thus obtained solution is sprayed on to kaolin, and the acetone subsequently evaporated in vacuo.

Wettable powder

The following constituents are used for the preparation of (a) a 40%, (b) a 50%, (c) a 25%, and (d) a 10% wettable powder:

a.
40 parts of 2-chloroethyl-(methyl-dioctyloxy)-silane,
5 parts of sodium lignin sulphonate,
1 part of sodium dibutyl-naphthalene sulphonate,
54 parts of silicic acid;

b.
50 parts of 2-chloroethyl- (methyl-di-dodecyloxy)-silane,
5 parts of alkylaryl sulphonate ("Tinovetin B"),
10 parts of calcium lignin sulphonate,
1 part of Champagne chalk/hydroxyethyl cellulose mixture (1 : .1),
20 parts of silicic acid,
14 parts of kaolin;

c.
25 parts of 2-chloroethyl-(methyl-di-4'-methoxy-benzoxy)-silane,
5 parts of the sodium salt of oleylmethyl tauride,
2.5 parts of naphthalenesulphonic acid/formaldehyde condensate,
0.5 parts of carboxymethyl cellulose,
5 parts of neutral potassium aluminum silicate,
62 parts of kaolin;

d.
10 parts of 2-chloroethyl- (methyl-di-4'-chlorobenzoxy)-silane
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives; the mixture is subsequently ground in suitable mills and rollers. Wettable powders are thus obtained which can be diluted with water to give suspensions of any desired concentration. Such suspensions are employed, e.g., for the removal of undesired side shoots, for the tillering of lawns, and for the rooting of seedlings and cuttings, etc..

EMULSION CONCENTRATE

The following constituents are mixed together to produce 25% emulsion concentrates:

a.
- 25 parts of 2-chloroethyl-(methyl-di-benzoxy)-silane,
- 5 parts of a mixture of nonylphenolpolyoxyethylene and calcium-dodecylbenzene sulphonate,
- 70 parts of xylene;

b.
- 25 parts of 2-chloroethyl-(methyl-di-ethoxy)-silane,
- 10 parts of a mixture of nonylphenolpolyoxyethylene and calcium-dodecylbenzene sulphonate,
- 65 parts of cyclohexanone.

This concentrate can be diluted with water to obtain emulsions of any desired concentration. Such emulsions are suitable for the thinning out of blossom and fruit, for the accelerated ripening of fruits, and for the promotion of fruit and leaf abscission.

We claim:

1. A silane according to the formula

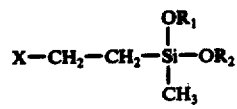

wherein X represents chlorine or bromine and $R_1$ and $R_2$ are identical and represent benzyl radicals, unsubstituted or mono-or polysubstituted in the phenyl ring by halogen, cyano, nitro, $C_1$-$C_4$ alkyl, $C_1$-$C_4$ alkoxy or $C_1$-$C_4$ alkylthio.

2. As silane according to claim 1 β-chloroethyl-methyl-bis-benzyloxy-silane.

3. As silane according to claim 1 β-chloroethyl-methyl-bis-(p-methoxybenzyloxy)-silane.

4. As silane according to claim 1 β-chloroethyl-methyl-bis-(p-chlorobenzyloxy)-silane.

5. As silane according to claim 1 β-chloroethyl-methyl-bis-(2'4'-dichlorobenzyloxy)-silane.

6. As silane according to claim 1 β-chloroethyl-methyl-bis-(p-methylbenzyloxy)-silane.

7. As silane according to claim 1 β-bromoethyl-methyl-bis-benzyloxy-silane.